(12) United States Patent
Campbell et al.

(10) Patent No.: US 7,355,094 B2
(45) Date of Patent: *Apr. 8, 2008

(54) METHODS OF UNGULATE NUCLEAR TRANSFER

(75) Inventors: Keith Henry Stockman Campbell, Midlothian (GB); Ian Wilmut, Midlothian (GB)

(73) Assignee: Roslin Institute (Edinburgh) (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/544,039

(22) Filed: Oct. 6, 2006

(65) Prior Publication Data

US 2007/0028313 A1      Feb. 1, 2007

Related U.S. Application Data

(60) Continuation of application No. 10/915,338, filed on Aug. 11, 2004, now Pat. No. 7,232,938, which is a continuation of application No. 09/225,233, filed on Jan. 4, 1999, which is a division of application No. 08/802,282, filed on Feb. 19, 1997, now Pat. No. 6,147,276, which is a continuation of application No. PCT/GB96/02099, filed on Aug. 30, 1996.

(30) Foreign Application Priority Data

Aug. 31, 1995   (GB)   ................. 9517780.4

(51) Int. Cl.
*C12N 15/00* (2006.01)
*A01K 67/027* (2006.01)

(52) U.S. Cl. ............................ 800/24; 800/15; 800/16; 800/17

(58) Field of Classification Search ................. 800/24, 800/14–18
See application file for complete search history.

(56) References Cited

U.S. PATENT DOCUMENTS

| | | | |
|---|---|---|---|
| 5,057,420 | A | 10/1991 | Massey |
| 5,496,720 | A | 3/1996 | Susko-Parrish et al. |
| 5,523,226 | A | 6/1996 | Wheeler |
| 5,945,577 | A | 8/1999 | Stice et al. |
| 6,147,276 | A | 11/2000 | Campbell et al. |
| 6,215,041 | B1 | 4/2001 | Stice et al. |
| 6,235,969 | B1 | 5/2001 | Stice et al. |
| 6,235,970 | B1 | 5/2001 | Stice et al. |
| 6,252,133 | B1 | 6/2001 | Campbell et al. |
| 6,525,243 | B1 | 2/2003 | Campbell et al. |
| 6,603,059 | B1 | 8/2003 | Strelchenko et al. |

FOREIGN PATENT DOCUMENTS

| | | |
|---|---|---|
| CA | 2092258 | 3/1993 |
| CA | 2059199 | 7/1993 |
| GB | 2265909 | 10/1993 |
| WO | WO A 94 06422 | 3/1994 |
| WO | WO A 95 03795 | 2/1995 |
| WO | WO 96 07732 | 9/1995 |

OTHER PUBLICATIONS

Czolowska et al., "Behavior of thymocyte nuclei in non-activated and activated mouse oocytes," *Journal of Cell Science*, vol. 69, see p. 27, line 1—p. 33, line 3; table 1 (1984).
Collas et al., "Factors affecting the efficiency of nuclear transplantation in the rabbit embryo," *Biology of Reproduction*, 43(5):877-884 (Nov. 1990).
Campbell et al., "Nuclear-cytoplasmic interactions during the first cycle of nuclear transfer reconstructed bovine embryos: implications from desoxyribonucleic acid replication and development," *Biology of Reproduction*, 49(1):933-942 (Nov. 1993).
Otaegui et al., "Transfer of nuclei from 8-cell stage mouse embryos following use of nocodazole to control the cell cycle," *Molecular Reproduction and Development*, 39(2):147-152 (Oct. 1, 1994).
Willadsen, "Nuclear transplantation in sheep embryos," *Nature*, 320(6), London, GB (Mar. 1986).
Greaham, "The fusion of cells with one and two-cell mouse embryo," The Wistar Institute Symposium Monograph, vol. 9:19 (Jan. 1, 1969).
Campbell et al., "Live lambs by nuclear transfer from an established cell line," *Theirogenology*, 45(1):287, ISSN: 0083-691X (1996).
Campbell et al., "Sheep cloned by nuclear transfer from a cultured cell line," *Nature*, 380:64 (Mar. 7, 1996).
Campbell, *Therio.*, 43:181 (1995).
Campbell, *Biol. Reprod.*, 49,933-942 (1993).
Campbell, *Biol. Reprod.*, 50:1385-1393 (1994).
Campbell, *J. Reprod. Fertil.* Abstract Series 5(32), Abstract No. 86 (1995).
Collas & Robl, *Biol. Reprod.*, 43:877-884 (1990).
Cutbertson & Cobbold, *Nature*, 316:541-542 (1985).
Finch, *Biochem Soc. Trans.*, 24:369S (1996).
Freeman & Beitz, In Symposium on Cloning Mammals by Nuclear Transplantation (Seidel, GE Jr. ed.), Colorado State University Colorado, pp. 17-20 (1992).
Gardner, *Biology of Reproduction*, 50:390-400 (1994).
Gurdon, *QJ Microsc. Soc.*, 101:299-311 (1960).
Kanka, *Mol. Reprod. Dev.*, 29:110-116 (1991).
Leno & Munshi, *J. Cell Biol.*, 127(1):5-14 (1994).
Prather & First, *J. Reprod. Fertil. Suppl.*, 41:125 (1990).
Prather, *Biol. Reprod.*, 37:859-866 (1987).
Richie et al., *J. Reprod. Fertil.* Abstract Series, 5(60), Abstract No. 175 (1995).

(Continued)

*Primary Examiner*—Deborah Crouch
(74) *Attorney, Agent, or Firm*—Finnegan, Henderson, Farabow, Garrett & Dunner, L.L.P.

(57) ABSTRACT

A method of reconstituting an animal embryo involves transferring the nucleus from a quiescent donor cell into a suitable recipient cell. The donor cell is quiescent, in that it is caused to exit from the growth and division cycle at G1 and to arrest in the G0 state. Nuclear transfer may take place by cell fusion. The reconstituted embryo may then give rise to one or more animals. The invention is useful in the production of transgenic animals as well as non-transgenics of high genetic merit.

20 Claims, No Drawings

OTHER PUBLICATIONS

Robertson, E.J., "*Teratocarcinomas & embryonic stem cells: a practical approach*," 71-112, IRL Press Oxford (1987).
Rob, Symposium on Cloning Mammals by Nuclear Transplantation (Seidel ed.) *Colorado State University*, pp. 24-27 (1992).
Smith & Wilmut, *Biol. Reprod.*, 40:1027-1035 (1989).
Thompson, *Biology of Reproduction*, 53:1385-1391 (1995).
Tsunoda, *J. Reprod. Fertil.*, 82:173 (1988).
Westhusin, *Biol. Reprod.* (Suppl.), 42:176, Abstract No. 407, (1990).
Wheeler, *Reprod. Fertil. Dev.*, 6:563-568 (1994).
Whitfield, *Control of Animal Cell Proliferation*, 1:331-365 (1985).
Whittingham & Wales, *Aust. J. Biol. Sci.*, 22:1065-1068 (1969).
Willadsen, *Nature*, 320(6):63-65 (1986).
Willadesen, In Mammalian Egg Transfer (Adams, E.E., ed.) 185, CRC Press, Boca Raton, Florida (1982).
Bradley, *Biotechnology*, 10:534-539 (1992).
Seamark, *Reprod. Fertil. & Devel.* 6(5):653, Abstract No. 95:4100 (1994).
Stanton, *Brain Physiology*, 2:71-73 (1992).
Tsunoda, *J. Reprod. & Fertil.*, 98:537-540 (1993).
Solter, *Nature*, 380:24-25 (1996).
Saito et al., *Develop. Biol.*, 201:134-141 (1992).
Briggs & King, *Proc. Nat'l. Acad. Sci. USA*, 38:455-461 (1952).
Campbell & Wilmut, *Vth World Congress on Genetics as Applied to Livestock*, 20:180-187 (1994).
Collas & Robl, *Biol. Reprod.*, 45:455-465 (1991).
Spemann, Embryonic Development & Induction, Hofner Publishing Co., New York, pp. 210-211 (1938).
Hoppe & Illmensee, *Proc. Nat'l Acad. Sci. USA*, 79:1912-1916 (1982).
Modlinski et al, *Development*, 108:337-348 (1990).
Illmensee & Hoppe, *Cell*, 23:9-18 (1981).
Prather et al., *Biology of Reproduction*, 41:414-418 (1989).
Hoppe & Illmensee, *Proc. Nat'l. Acad. Sci. USA*, 74:5657-5661 (1977).
DiBerardino et al. , *Science*, 219:862-862 (1983).
DiBerardino et al., *Science*, 224:946-952 (1984).
DiBerardino et al., *Proc. Nat'l. Acad. Sci, USA*, 83:8231-8234 (1986).
Prather, *Proc. of the Society for Experimental Biology and Medicine*, 195(1):7-12 (1990).
Prather et al., *J. Reprod. Fert.*, Suppl. 40:227-234 (1990).
DiBerardino, *Genomic Potential of Differentiated Cells*, Columbia University Press, Chapter 6, p. 84 (1997).
DiBerardino, *Genomic Potential of Differentiated Cells*, Columbia University Press, Chapter 10, p. 206 (1997).
Surani et al., *Biol. Reprod.*, 36:1-16 (1987).
McGrath et al., *Science*, 220:1300-1302 (1983).
Costlow et al., *J. Cell. Physiol.*, 82(2):411-419 (1973).
Campisi et al., *Exp. Cell Res.*, 152:459-466 (1984).
Briggs et al., *Proc. Nat'l. Acad. Sci. USA*, 38:455-461 (1952).
Darzynkiewicz, "The Cell Cycle: A Practical Approach," eds. P. Fantes, R. Brooks, Oxford University Press, New York, pp. 45-68 (1993).
Van Putten, *Biomedicine*, 20(1):5-8 (1974).
Campisi et al., *Science*, 219:862-862 (1983).
Larsson et al., *J. Cell. Physiol.*, 127:267-273 (1986).
Holm et al., "Embryo viability, duration of gestation and birth weight in sheep after transfer of in vitro matured and in vitro fertilized zygotes cultured in vitro or in vivo," *J. Reproduction and Fertility*, 107:175-181 (1996).
Holm et al., "In vitro and in vivo development of cloned ovine embryos using in vitro and in vivo matured oocytes," *Reprod. Dom. Anim.*, 30:125-128 (1995).
Watson et al., "Progesterone and estrogen receptor distribution in the endometrium of the mare," *Theriogenology*, 38:575-580 (1992).
McLaughlin et al., "In vitro embryo culture in the production of identical merino lambs by nuclear transplantation," *Reprod. Fertil. Dev.*, 2:619-622 (1990).

Walker et al., "In vitro assessment of the viability of sheep zygotes after pronuclear microinjection," *Reprod. Fertil. Dev.*, 2:633-640 (1990).
Seamark, "Efficient creation of transgenic sheep: the challenge for the cell biologist," *The Biology of Wool and Hair*, eds. G.E. Rogers et al., Chapman and Hall, 479-488 (1988).
Daw, "SA calf cloning success will aid disease fight," *The Advertiser*, Australia (Oct. 24, 1990).
Walker et al., "Culture of embryos of farm animals," *Embryonic Development and Manipulation in Animal Production*, eds. A. Lauria & F. Gandolfi, Portland Press, 77-92 (1992).
Seamark, "Embryo multiplication—present status of nuclear transfer and embryonic stem cell technology in livestock," *Med. Fac. Landbouww Univ. Ghent*, 57/4b:1837-1842 (1992).
Vize et al., "Introduction of a porcine growth hormone fusion gene into transgenic pigs promotes growth," (1988).
Seamark, "Progress and emerging problems in livestock transgenesis: a summary perspective," *Reprod. Fertil. Dev.*, 6:653-657 (1994).
McLaughlin, "Factors in the production of identical animals by nuclear transfer," Thesis submitted to Department of Obstetrics and Gynaecology, The University of Adelaide (Jan. 1991).
Evans et al., "Mitochondrial DNA Genotypes in nuclear transfer-derived cloned sheep," *Nature Genetics*, 23:90-93 (Sep. 1999).
Meade et al., "Bovine alpha s-1-casein gene sequences direct high level expression of active human urokinase in mouse milk," *Bio/Technology*, 8:443-446 (May 1990).
Simons et al., "Gene transfer into sheep," *Bio/Technology*, 6:179-183 (Feb. 1988).
Elbert et al., "Transgenic production of a variant of human tissue-type plasminogen activator in goat milk: generation of transgenic goats and analysis of expression," *Bio/Technology*, 9:835-838 (Sep. 1991).
Massoud et al., "Expression of active recombinant human alpha 1-antitrypsin in transgenic rabbits," *Journal of Bio/Technology*, 18:193-204 (1991).
Velander et al., "High-level expression of a heterologous protein in the milk of transgenic swine using the cDNA encoding human protein C," *Proc. Natl. Acad. Sci. USA*, 89:12003-12007 (Dec. 1992).
Cheong et al., "Birth of mice after transplantation of early cell-cycle stage embronic nuclei into enucleated oocytes," *Biology of Reproduction*, 48:958-963 (1993).
Yang et al., "Nuclear totipotency of cultured rabbit morulae to support full-term development following nuclear transfer," *Biology of Reproduction*, 47:636-643 (1992).
Sims et al., "Production of calves by transfer of nuclei from cultured inner cell mass cells," *Proc. Natl. Acad. Sci.*, 90:6143-6147 (Jun. 1993).
Hyttinen et al., "Generation of transgenic dairy cattle from transgene-analyzed and sexed embryos produced in vitro," *Bio/Technology*, 12 (Jun. 1994).
Yong, et al., "Nuclear Transplantation in Goats," vol. 35, No. 1 (Jan. 1991).
Brosselman et al., *Science*, 243:533-535 (1989).
Fehilly et al., *Nature*, 307:634-636 (1984).
Fehilly et al., *J. Repro. Fert.*, 74:215-222 (1985).
Fulka et al., *BioEssays*, 20:847-851 (1998).
Kono, *Rev. Reprod.*, 2:74-80 (1997).
Wolf et al., *J. Biotech.*, 65:99-110 (1998).
Araki et al., "Site-specific recombination of a transgene in fertilized eggs by transient expression of Cre recombinase," *Pro., Natl. Acad. Sci., USA*, 92:160-164 (Jan. 1995).
Pennisi and Vogel, "Cloning: A Hard Act to Follow," *Science*, 288:1722-1727 (Jun. 2000).
Mitalipov et al., "Rhesus Monkey Embryos Produced by Nuclear Transfer from Embryonic Blastomeres or Somatic Cells," *Biology of Reproduction*, 66:1367-1373 (2002).
Seike et al., "Identical Twin Calves of Different Ages," *J. Vet. Med. Sci.*, 53:37-42 (1991).
Morris et al., "Effect of Immunization Against Synthetic Peptide Sequences of Bovine Inhibin Alpha-Subunit on Ovulation Rate and Twin-Calving Rate in Heifers," *J. Reprod. Fert.*, 97:225-261 (1993).

Salamonsen et al., "Production of Matrix Metalloproteinase 3 (Stromelysin) by Cultured Ovine Endometrial Cells," *J. Cell Sci.*, 100:381-385 (1991).

D'Anrea et al., "Paracrine Activities of Porcine Trophoblastic Interferons," *J. Reprod. Fert.*, 102:185-194 (1994).

Barker et al., "Hemoglobin Switching in Sheep and Goats: Erythropoietin-Dependent Synthesis of Hemoglobin C in Goat Bone-Marrow Cultures," *Proc. Natl, Acad. Sci.*, 70(6):1739-1743 (1973).

Yoshimura et al., "Transfection of Beta-Casein Chimeric Gene and Hormonal Induction of its Expression in Primary Murine Mammary Epithelial Cells," *Proc. Natl., Acad. Sci.* (USA), 87:3670-3674 (1990).

Adolphe et al., "Cell Multiplication and Type II Collagen Production by Rabbit Articular Chondrocytes Cultivated in a Defined Medium," *Exp. Cell Res.*, 1994 155:527-536.

Stirling et al., "Angiotensin II Inhibits Lutenizing Hormone-Stimulated Cholesterol Side Chain Cleavage Expression and Stimulates Basic Fibroblast Growth Factor Expression in Bovine Luteal Cells in Primary Culture," *Biol. Chem.*, 265:5-8 (1990).

*Molecular Biology of the Gene*, 4$^{th}$ Ed., Watson et al., The Benjamin/Cummings Publishing Company, Menlo Park, CA, 1987, pp. 9-10.

Lawrence et al., "Feeding Status Affects Glucose Metabolism in Exercising Horses," *The Journal of Nutrition*, 123(1):2152-2157 (Dec. 1993).

Gonzales-Pacheco et al., "Energy Restriction Reduces Metabolic Rates in Adult Male Fisher-344 Rats," *The Journal of Nutrition*, 123(1):90-97 (1993).

Fitchev et al., "Nuclear Transfer in the Rat: Potential Access to the Germline," *Transplantation Proceed.*, 31:1525-1530 (1999).

Chense et al., "Cloned Rabbits Produced by Nuclear Transfer from Adult Somatic Cells," *Nature Biotechnology*, 20:366-369 (2002).

Galli et al., "A Clones Horse Born to its Dam Twin," *Nature*, 424:635 (2003).

Wakayama et al., "Full-Term Development of Mice from Enucleated Oocytes Injected with Cumulus Cell Nuclei," *Nature*, 394:369-374 (1998).

Zhou et al., "Generation of Fertile Clones Rats by Regulating Oocyte Activation," *Science.*, 302:1179 (1998).

METHODS OF UNGULATE NUCLEAR TRANSFER

This is a continuation of application Ser. No. 10/915,338, filed Aug. 11, 2004, now U.S. Pat. No. 7,232,938 which is a continuation of application Ser. No. 09/225,233, filed Jan. 4, 1999, which is a division of application Ser. No. 08/802,282, filed Feb. 19, 1997 (now U.S. Pat. No. 6,147,276), which is a continuation of International Application No. PCT/GB96/02099, filed Aug. 30, 1996. All of these applications are incorporated by reference.

This invention relates to the generation of animals including but not being limited to genetically selected and/or modified animals.

The reconstruction of mammalian embryos by the transfer of a nucleus from a donor embryo to an enucleated oocyte or one cell zygote allows the production of genetically identical individuals. This has clear advantages for both research (i.e. as biological controls) and also in commercial applications (i.e. multiplication of genetically valuable livestock, uniformity of meat products, animal management). One problem with the use of early embryos as nuclear donors is that the number of offspring which can be produced from a single embryo is limited both by the number of cells (embryos at the 32-64 cell stage are the most widely used in farm animal species) and the efficiency of the nuclear transfer protocol.

In contrast to the use of embryos as nuclear donors, the ability to produce live offspring by nuclear transfer from cells which can be maintained in culture is an objective which have been sought for some time by animal breeders. The ability to produce cloned offspring from a cultured cell line would offer a large number of advantages over the use of early embryos. These include: the production of large numbers of identical offspring over a long time period (cultured cells can be frozen and stored) and the ability genetically to modify and/or select cell populations of the required genotype (e.g. sex) prior to embryo reconstruction. One potential cell type for use in these procedures is the Embryonic Stem (ES) cell. ES cells have been isolated in the mouse, however as yet there are no reports of development to term following their use in nuclear transfer. At the present time there is a single report of ES like cells in pig which have contributed to development following injection into the blastocoele cavity of in vivo-produced blastocysts (Wheeler, *Reprod. Fertil. Dev.* 6 563-568 (1994)) but no reports of chimerism in other farm livestock species and no reports of development to term following nuclear transfer in any mammalian species from any established cell line.

There are several alternatives to the use of ES cell lines; one of these is to search for other cell populations which are able to promote development when used for nuclear transfer. Several reports have suggested that Primordial Germ Cells offer a suitable candidate; however no development to term has yet been reported. Cell lines established from early embryos have been suggested; although development has been reported from early passage cells in the sheep (Campbell et al., *Therio* 43 181 (1995)) on prolonged culture, no development was obtained using conventional nuclear transfer protocols (Campbell et al., *J. Abstract Series* (5) 31 (1995)).

In order to obtain development to term after nuclear transfer the developmental clock of the transferred nucleus must be reset. For this to occur transcription must be arrested and then restarted in a developmentally regulated pattern. Previous reports have shown that development to the blastocyst stage can be obtained from a wide range of cell types in the cow, sheep, pig, rabbit and mouse. However, in all of these reports no development to term has been reported. The birth of live lambs following nuclear transfer from primary cell lines (up to and including passage 3) which were established from the embryonic disc (ED) of day 9 ovine embryos has previously been reported (Campbell et al., *Therio* 43 181 (1995)). However, on subsequent culture no development to term was obtained using conventional nuclear transfer protocols (at passage 6 and 11) (Campbell et al., *J. Reprod. Fertil. Abstract Series* (5) 31 (1995)). These results can be interpreted in a number of ways; firstly it can be postulated that all of the ED derived cells obtained during early periods of culture are able to promote development. However, on prolonged culture during establishment of a cultured cell line these cells change and are thus unable to control development when used as nuclear donors for nuclear transfer into the "Universal Recipient" referred to in the above papers. Alternatively it may be postulated that during the early culture period a sub-population of cells retains the ability to promote development and that this would explain the production of live offspring following nuclear transfer during these early passages. Previous studies have emphasised the role of cell cycle co-ordination of the donor nucleus and the recipient cytoplasm in the development of embryos reconstructed by nuclear transfer (Campbell et al., *Biol. Reprod.* 49 933-942 (1993) and *Biol. Reprod.* 50 1385-1393 (1994)).

Two possible alternative strategies to that of relying on the isolation of a cell line which is totipotent for nuclear transfer using published nuclear transfer protocols are:

(1) to modify existing nuclear transfer procedures; or
(2) to modify the chromatin of the donor cell prior to nuclear transfer.

A totipotent cell can direct the development of a whole animal (when constructing embryos by nuclear transfer from a donor cell into a recipient cell, such as an enucleated oocyte, it is the nucleus of the donor cell which is totipotent). This includes directing the development of extra-embryonic lineages, i.e. the placenta. In this definition, a fertilised zygote and in some species individual blastomeres are also totipotent. In contradistinction, a pluripotent or multipotent cell (i.e. an embryonic stem cell) type has been defined as one which can form all tissues in the conceptus/offspring after injection into the blastocoele cavity.

In both the nuclear transfer strategies (1) and (2) outlined above, a method is required which will allow the reprogramming of gene expression of the transferred nucleus: such a method would then allow the use of differentiated or partially differentiated cells as nuclear donors and would "bring out" their inherent totipotency.

It has now been found that quiescent cells, that is to say cells which are not actively proliferating by means of the cell cycle, can advantageously be used as nuclear donors in the reconstitution of an animal embryo. Such embryos may then be allowed to develop to term. It seems that changes in the donor nucleus which are observed after embryo reconstruction and which are required for efficient nuclear transfer can be induced in the nuclei of cells prior to their use as nuclear donors by causing them to enter the quiescent state. This fact has been exploited in the present application.

According to a first aspect of the present invention, there is provided a method of reconstituting an animal embryo, the method comprising transferring the nucleus of a quiescent donor cell into a suitable recipient cell.

In principle, the invention is applicable to all animals, including birds, such as domestic fowl, amphibian species and fish species. In practice, however, it will be to non-human animals, especially (non-human) mammals, particularly placental mammals, that the greatest commercially useful applicability is presently envisaged. It is with ungulates, particularly economically important ungulates such as cattle, sheep, goats, water buffalo, camels and pigs that the invention is likely to be most useful, both as a means for cloning animals and as a means for generating transgenic or genetically modified animals. It should also be noted that the invention is also likely to be applicable to other economically important animal species such as, for example, horses, llamas or rodents e.g. rats or mice, or rabbits.

The invention is equally applicable in the production of transgenic, as well as non-transgenic animals. Transgenic animals may be produced from genetically altered donor cells. The overall procedure has a number of advantages over conventional procedures for the production of transgenic (i.e. genetically modified) animals which may be summarised as follows:

(1) fewer recipients will be required;
(2) multiple syngeneic founders may be generated using clonal donor cells;
(3) subtle genetic alteration by gene targeting is permitted;
(4) all animals produced from embryos prepared by the invention should transmit the relevant genetic modification through the germ line as each animal is derived from a single nucleus; in contrast, production of transgenic animals by pronuclear injection or chimerism after inclusion of modified stem cell populations by blastocyst injection, or other procedures, produces a proportion of mosaic animals in which all cells do not contain the modification and the resultant animal may not transmit the modification through the germ line; and
(5) cells can be selected for the site of genetic modification (e.g. integration) prior to the generation of the whole animal.

It should be noted that the term "transgenic", in relation to animals, should not be taken to be limited to referring to animals containing in their germ line one or more genes from another species, although many transgenic animals will contain such a gene or genes. Rather, the term refers more broadly to any animal whose germ line has been the subject of technical intervention by recombinant DNA technology. So, for example, an animal in whose germ line an endogenous gene has been deleted, duplicated, activated or modified is a transgenic animal for the purposes of this invention as much as an animal to whose germ line an exogenous DNA sequence has been added.

In embodiments of the invention in which the animal is transgenic, the donor nucleus is genetically modified. The donor nucleus may contain one or more transgenes and the genetic modification may take place prior to nuclear transfer and embryo reconstitution. Although micro-injection, analogous to injection into the male or female pronucleus of a zygote, may be used as a method of genetic modification, the invention is not limited to that methodology: mass transformation or transfection techniques can also be used e.g. electroporation, viral transfection or lipofection.

In the method of the invention described above, a nucleus is transferred from a quiescent donor cell to a recipient cell. The use of this method is not restricted to a particular donor cell type. All cells of normal karyotype, including embryonic, foetal and adult somatic cells, which can be induced to enter quiescence or exist in a quiescent state in vivo may prove totipotent using this technology. The invention therefore contemplates the use of an at least partially differentiated cell, including a fully differentiated cell. Donor cells may be, but do not have to be, in culture. Cultured bovine primary fibroblasts, an embryo-derived ovine cell line (TNT4), an ovine mammary epithelial cell derived cell line (OME) from a 6 year old adult sheep, a fibroblast cell line derived from foetal ovine tissue (BLWF1) and an epithelial-like cell line derived from a 9-day old sheep embryo (SEC1) are exemplified below. A class of embryo-derived cell lines useful in the invention which includes the TNT4 cell line are also the subject of co-pending PCT Patent Application No. PCT/GB95/02095, published as WO96/07732.

To be useful in the invention, donor cells are quiescent, which is to say that they are not actively proliferating by means of the mitotic cell cycle. The mitotic cell cycle has four distinct phases, G1, S, G2 and M. The beginning event in the cell cycle, called start, takes place in the G1 phase and has a unique function. The decision or commitment to undergo another cell cycle is made at start. Once a cell has passed through start, it passes through the remainder of the G1 phase, which is the pre-DNA synthesis phase. The second stage, the S phase, is when DNA synthesis takes place. This is followed by the G2 phase, which is the period between DNA synthesis and mitosis. Mitosis itself occurs at the M phase. Quiescent cells (which include cells in which quiescence has been induced as well as those cells which are naturally quiescent, such as certain fully differentiated cells) are generally regarded as not being in any of these four phases of the cycle; they are usually described as being in a G0 state, so as to indicate that they would not normally progress through the cycle. The nuclei of quiescent G0 cells have a diploid DNA content.

Cultured cells can be induced to enter the quiescent state by various methods including chemical treatments, nutrient deprivation, growth inhibition or manipulation of gene expression. Presently the reduction of serum levels in the culture medium has been used successfully to induce quiescence in both ovine and bovine cell lines. In this situation, the cells exit the growth cycle during the G1 phase and arrest, as explained above, in the so-called G0 stage. Such cells can remain in this state for several days (possibly longer depending upon the cell) until re-stimulated when they re-enter the growth cycle.

Quiescent cells arrested in the G0 state are diploid. The G0 state is the point in the cell cycle from which cells are able to differentiate. On quiescence a number of metabolic changes have been reported and these include: monophosphorylated histones, ciliated centrioles, reduction or complete cessation in all protein synthesis, increased proteolysis, decrease in transcription and increased turnover of RNA resulting in a reduction in total cell RNA, disaggregation of polyribosomes, accumulation of inactive 80S ribosomes and chromatin condensation (reviewed Whitfield et al., *Control of Animal Cell Proliferation,* 1 331-365 (1985)).

Many of these features are those which are required to occur following transfer of a nucleus to an enucleated oocyte. The fact that the G0 state is associated with cell differentiation suggests that this may provide a nuclear/chromatin structure which is more amenable to either remodelling and/or reprogramming by the recipient cell cytoplasm. In this way, by virtue of the nuclear donor cells being in the quiescent state, the chromatin of the nuclei of the donors may be modified before embryo reconstitution or reconstruction such that the nuclei are able to direct development. This differs from all previously reported methods of nuclear transfer in that the chromatin of donor cells is modified prior to the use of the cells as nuclear donors.

The recipient cell to which the nucleus from the donor cell is transferred may be an oocyte or another suitable cell.

Recipient cells at a variety of different stages of development may be used, from oocytes at metaphase I through metaphase II, to zygotes and two-cell embryos. Each has its advantages and disadvantages. The use of fertilized eggs ensures efficient activation whereas parthenogenetic activation is required with oocytes (see below). Another mechanism that may favour the use of cleavage-stage embryos in some species is the extent to which reprogramming of gene expression is required. Transcription is initiated during the second cell cycle in the mouse and no major changes in the nature of the proteins being synthesised are revealed by two-dimensional electrophoresis until the blastocyst stage (Howlett & Bolton *J. Embryol. Exp. Morphol.* 87 175-206 (1985)). In most cases, though, the recipient cells will be oocytes.

It is preferred that the recipient be enucleate. While it has been generally assumed that enucleation of recipient oocytes in nuclear transfer procedures is essential, there is no published experimental confirmation of this judgement. The original procedure described for ungulates involved splitting the cell into two halves, one of which was likely to be enucleated (Willadsen *Nature* 320 (6) 63-65 (1986)). This procedure has the disadvantage that the other unknown half will still have the metaphase apparatus and that the reduction in volume of the cytoplasm is believed to accelerate the pattern of differentiation of the new embryo (Eviskov et al., *Development* 109 322-328 (1990)).

More recently, different procedures have been used in attempts to remove the chromosomes with a minimum of cytoplasm. Aspiration of the first polar body and neighbouring cytoplasm was found to remove the metaphase II apparatus in 67% of sheep oocytes (Smith & Wilmut *Biol. Reprod.* 40 1027-1035 (1989)). Only with the use of DNA-specific fluorochrome (Hoechst 33342) was a method provided by which enucleation would be guaranteed with the minimum reduction in cytoplasmic volume (Tsunoda et al., *J. Reprod. Fertil.* 82 173 (1988)). In livestock species, this is probably the method of routine use at present (Prather & First *J. Reprod. Fertil. Suppl.* 41 125 (1990), Westhusin et al., *Biol. Reprod. (Suppl.)* 42 176 (1990)).

There have been very few reports of non-invasive approaches to enucleation in mammals, whereas in amphibians, irradiation with ultraviolet light is used as a routine procedure (Gurdon Q. J. *Microsc. Soc.* 101 299-311 (1960)). There are no detailed reports of the use of this approach in mammals, although during the use of DNA-specific fluorochrome it was noted that exposure of mouse oocytes to ultraviolet light for more than 30 seconds reduced the developmental potential of the cell (Tsunoda et al., *J. Reprod. Fertil.* 82 173 (1988)).

It is preferred that recipient host cells to which the donor cell nucleus is transferred is an enucleated metaphase II oocyte, an enucleated unactivated oocyte or an enucleated preactivated oocyte. At least where the recipient is an enucleated metaphase II oocyte, activation may take place at the time of transfer. Alternatively, at least where the recipient is an enucleated unactivated metaphase II oocyte, activation may take place subsequently. As described above enucleation may be achieved physically, by actual removal of the nucleus, pro-nuclei or metaphase plate (depending on the recipient cell), or functionally, such as by the application of ultraviolet radiation or another enucleating influence.

Three suitable cytoplast (enucleated oocyte) recipients are:
1. The "MAGIC Recipient" (Metaphase Arrested G1/G0 AcceptIng Cytoplast) described in our co-pending PCT patent application No. PCT/GB96/02098 filed today (claiming priority from GB 9517779.6).
2. The "GOAT" (G0/G1 Activation and Transfer)—a MII (metaphase II) oocyte at the time of activation (Campbell et al., *Biol. Reprod.* 49 933-942 (1993).
3. The "Universal Recipient" (Campbell et al., *Biol. Reprod.* 649 933-942 (1993), *Biol. Reprod.* 50 1385-1393 (1994).

All three of these recipients would result in normal ploidy when using donor nuclei in G0 in the reconstructed embryo. However, recent reports have suggested that a proportion of the nuclei from quiescent cells are unable to enter the DNA synthetic phase when placed into an S-phase cytoplasm without undergoing disassembly of the nuclear envelope (Leno & Munshi, *J. Cell Biol.* 127(1) 5-14 (1994)). Therefore, although a proportion of embryos will develop when using the "Universal Recipient" it is postulated that the use of MII oocytes containing high levels of MPF (M-phase promoting factor or maturation-promoting factor) as cytoplast recipients by either method 1 or 2 will result in a greater frequency of development.

Once suitable donor and recipient cells have been identified, it is necessary for the nucleus of the former to be transferred to the latter. Most conveniently, nuclear transfer is effected by fusion.

Three established methods which have been used to induce fusion are:
(1) exposure of cells to fusion-promoting chemicals, such as polyethylene glycol;
(2) the use of inactivated virus, such as Sendai virus; and
(3) the use of electrical stimulation.

Exposure of cells to fusion-promoting chemicals such as polyethylene glycol or other glycols is a routine procedure for the fusion of somatic cells, but it has not been widely used with embryos. As polyethylene glycol is toxic it is necessary to expose the cells for a minimum period and the need to be able to remove the chemical quickly may necessitate the removal of the zona pellucida (Kanka et al., *Mol. Reprod. Dev.* 29 110-116 (1991)). In experiments with mouse embryos, inactivated Sendai virus provides an efficient means for the fusion of cells from cleavage-stage embryos (Graham *Wistar Inst. Symp. Monoqr.* 9 19 (1969)), with the additional experimental advantage that activation is not induced. In ungulates, fusion is commonly achieved by the same electrical stimulation that is used to induce pathogenetic activation (Willadsen *Nature* 320 (6) 63-65 (1986), Prather et al., *Biol. Reprod.* 37 859-866 (1987)). In these species, Sendai virus induces fusion in a proportion of cases, but is not sufficiently reliable for routine application (Willadsen *Nature* 320 (6) 63-65 (1986)).

While cell-cell fusion is a preferred method of effecting nuclear transfer, it is not the only method that can be used. Other suitable techniques include microinjection (Ritchie and Campbell, *J. Reproduction and Fertility* Abstract Series No. 15, p60).

Before or (preferably) after nuclear transfer (or, in some instances at least, concomitantly with it), it is generally necessary to stimulate the recipient cell into development by parthenogenetic activation, at least if the cell is an oocyte. Recent experiments have shown that the requirements for parthogenetic activation are more complicated than had been imagined. It had been assumed that activation is an all-or-none phenomenon and that the large number of treatments able to induce formation of a pronucleus were all causing "activation". However, exposure of rabbit oocytes to repeated electrical pulses revealed that only selection of an appropriate series of pulses and control of the $Ca^{2+}$ was able to promote development of diploidized oocytes to mid-gestation (Ozil Development 109 117-127 (1990)). During fertilization there are repeated, transient increases in intracellular calcium concentration (Cutbertson & Cobbold Nature 316 541-542 (1985)) and electrical pulses are believed to cause analogous increases in calcium concentration. There is evidence that the pattern of calcium transients varies with species and it can be anticipated that the optimal pattern of electrical pulses will vary in a similar manner. The interval between pulses in the rabbit is approximately 4 minutes (Ozil Development 109 117-127 (1990)), and in the mouse 10 to 20 minutes (Cutbertson & Cobbold Nature 316 541-542 (1985)), while there are preliminary observations in the cow that the interval is approximately 20 to 30 minutes (Robl et al., in Symposium on cloning Mammals by Nuclear Transplantation (Seidel ed.), Colorado State University, 24-27 (1992)). In most published experiments activation was induced with a single electrical pulse, but new observations suggest that the proportion of reconstituted embryos that develop is increased by exposure to several pulses (Collas & Robl Biol. Reprod. 43 877-884 (1990)). In any individual case, routine adjustments may be made to optimise the number of pulses, the field strength and duration of the pulses and the calcium concentration of the medium.

According to a second aspect of the present invention there is provided a reconstituted animal embryo prepared by a method as described previously.

According to a third aspect of the present invention there is provided a method for preparing an animal, the method comprising:

(a) reconstituting an animal embryo as described above; and (b) causing an animal to develop to term from the embryo; and (c) optionally, breeding from the animal so formed.

Step (a) has been described in depth above.

The second step, step (b) in the method of this aspect of the invention is to cause an animal to develop to term from the embryo. This may be done directly or indirectly. In direct development, the reconstituted embryo from step (a) is simply allowed to develop without further intervention beyond any that may be necessary to allow the development to take place. In indirect development, however, the embryo may be further manipulated before full development takes place. For example, the embryo may be split and the cells clonally expanded, for the purpose of improving yield.

Alternatively or additionally, it may be possible for increased yields of viable embryos to be achieved by means of the present invention by clonal expansion of donors and/or if use is made of the process of serial (nuclear) transfer. A limitation in the presently achieved rate of blastocyst formation may be due to the fact that a majority of the embryos do not "reprogram" (although an acceptable number do). If this is the case, then the rate may be enhanced as follows. Each embryo that does develop itself can be used as a nuclear donor, such as, for example at the morula or 32-64 cell stage; alternatively, inner cell mass cells can be used at the blastocyst stage. Embryos derived from these subsequent transfers could themselves also be used as potential nuclear donors to further increase efficiency. If these embryos do indeed reflect those which have reprogrammed gene expression and those nuclei are in fact reprogrammed (as seems likely), then each developing embryo may be multiplied in this way by the efficiency of the nuclear transfer process. The degree of enhancement likely to be achieved depends upon the cell type. In sheep, it is readily possible to obtain 55% blastocyst stage embryos by transfer of a single blastomere from a 16 cell embryo to a preactivated "Universal Recipient" oocyte. So it is reasonable to hypothesise that each embryo developed from a single cell could give rise to eight at the 16 cell stage. Although these figures are just a rough guide, it is clear that at later developmental stages the extent of benefit would depend on the efficiency of the process at that stage.

It is also contemplated that a new cell line to act as a source of nuclear donor cells could be produced from embryos formed according to the preceding description or the resulting foetuses or adults.

In certain instances, where there may be restrictions in the development of a reconstructed embryo to term it may be preferable to generate a chimeric animal formed from cells derived from a naturally formed embryo and an embryo reconstructed by nuclear transfer. Such a chimera can be formed by taking a proportion of cells of the natural embryo and a proportion of the cells of the reconstructed embryo at any stage up to the blastocyst stage and forming a new embryo by aggregation or injection. The proportion of cells may be in the ratio of 50:50 or another suitable ratio to achieve the formation of an embryo which develops to term. The presence of normal cells in these circumstances is thought to assist in rescuing the reconstructed embryo and allowing successful development to term and a live birth.

Aside from the issue of yield-improving expediencies, the reconstituted embryo may be cultured, in vivo or in vitro to blastocyst.

Experience suggests that embryos derived by nuclear transfer are different from normal embryos and sometimes benefit from or even require culture conditions in vivo other than those in which embryos are usually cultured (at least in vivo). The reason for this is not known. In routine multiplication of bovine embryos, reconstituted embryos (many of them at once) have been cultured in sheep oviducts for 5 to 6 days (as described by Willadsen, In Mammalian Egg Transfer (Adams, E. E., ed.) 185 CRC Press, Boca Raton, Fla. (1982)). In the practice of the present invention, though, in order to protect the embryo it should preferably be embedded in a protective medium such as agar before transfer and then dissected from the agar after recovery from the temporary recipient. The function of the protective agar or other medium is twofold: first, it acts as a structural aid for the embryo by holding the zona pellucida together; and secondly it acts as barrier to cells of the recipient animal's immune system. Although this approach increases the proportion of embryos that form blastocysts, there is the disadvantage that a number of embryos may be lost.

If in vitro conditions are used, those routinely employed in the art are quite acceptable.

At the blastocyst stage, the embryo may be screened for suitability for development to term. Typically, this will be done where the embryo is transgenic and screening and selection for stable integrants has been carried out. Screening for non-transgenic genetic markers may also be carried out at this stage. However, because the method of the invention allows for screening of donors at an earlier stage, that will generally be preferred.

After screening, if screening has taken place, the blastocyst embryo is allowed to develop to term. This will generally be in vivo. If development up to blastocyst has taken place in vitro, then transfer into the final recipient animal takes place at this stage. If blastocyst development has taken place in vivo, although in principle the blastocyst can be allowed to develop to term in the pre-blastocyst host, in practice the blastocyst will usually be removed from the (temporary) pre-blastocyst recipient and, after dissection from the protective medium, will be transferred to the (permanent) post-blastocyst recipient.

In optional step (c) of this aspect of the invention, animals may be bred from the animal prepared by the preceding steps. In this way, an animal may be used to establish a herd or flock of animals having the desired genetic characteristic(s).

Animals produced by transfer of nuclei from a source of genetically identical cells share the same nucleus, but are not strictly identical as they are derived from different oocytes. The significance of this different origin is not clear, but may affect commercial traits. Recent analyses of the mitochondrial DNA of dairy cattle in the Iowa State University Breeding Herd revealed associated with milk and reproductive performance (Freeman & Beitz, In Symposium on Cloning Mammals by Nuclear Transplantation (Seidel, G. E. Jr., ed.) 17-20, Colorado State University, Colorado (1992)). It remains to be confirmed that similar effects are present throughout the cattle population and to consider whether it is possible or necessary in specific situations to consider the selection of oocytes. In the area of cattle breeding the ability to produce large numbers of embryos from donors of high genetic merit may have considerable potential value in disseminating genetic improvement through the national herd. The scale of application will depend upon the cost of each embryo and the proportion of transferred embryos able to develop to term.

By way of illustration and summary, the following scheme sets out a typical process by which transgenic and non-transgenic animals may be prepared. The process can be regarded as involving seven steps:

(1) selection and isolation of suitable donor cells, which may include assessment of karyotype, induction of quiescence (arrest in G0) and/or induction of development;

(2) application of suitable molecular biological techniques for the production of genetically modified cell populations. Such techniques may include gene additions, gene knock-outs, gene knock-ins, and other gene modifications optionally, transgenesis, may also be employed by transfection with suitable constructs, with or without selectable markers;

(3) optionally screen and select modified cell populations or clones for the required genotype/phenotype (i.e. stable integrants);

(4) induction of quiescence in modified cell population;

(5) embryo reconstitution by nuclear transfer;

(6) culture, in vivo or in vitro, to blastocyst;

(6a) optionally screen and select for stable integrants—omit if done at (3)—or other desired characteristics;

(7) transfer if necessary to final recipient.

According to a fourth aspect of the invention, there is provided an animal prepared as described above.

Preferred features for each aspect of the invention are as for each other aspect, *mutatis mutandis*.

The present invention will now be described by reference to the accompanying Examples which are provided for the purposes of illustration and are not to be construed as being limiting on the present invention.

EXAMPLES

Example 1

Induction of Quiescence in Donor Cells

Various methods have been shown to induce quiescence in cultured cell lines, including; contact inhibition or serum starvation (reviewed Whitfield et al., *Control of Animal Cell Proliferation*, 1 331-365 (1985)). The method of induction of quiescence is not thought to be of importance, the important step is that the cells exit the growth cycle, arrest in a G0 state with a diploid DNA content and remain viable. In Examples 3 and 4, serum starvation of bovine primary fibroblasts, a bovine cell line established from the inner cell mass of day 7 in vivo produced blastocysts, and an embryo derived ovine cell line (TNT4), was used to induce quiescence and arrest the cells in the G0 phase of the cell cycle. Serum starvation was similarly used to induce quiescence of the donor cells described in Example 5.

Example 2

Isolation of Oocytes and Nuclear Transfer

Oocytes can be obtained by (i) in vitro maturation of slaughterhouse material, or from transvaginal follicle puncture; (ii) in vivo maturation and surgically recovery; or (iii) any other suitable procedure. All in vivo matured oocytes should be harvested by flushing from the oviduct in calcium magnesium free phosphate buffered saline (PBS) containing 1.0% foetal calf serum (FCS). In vitro matured oocytes are harvested and transferred to calcium free M2 (Whittingham and Wales *Aust. J. Biol. Sci.* 22 1065-1068 (1969)) containing 1.0% FCS. Oocytes are denuded of cumulus cells and enucleated as previously described (Campbell et al., *Biol. Reprod.* 49 933-942 (1993) and *Biol. Reprod.* 50 1385-1393 (1994)) with the exception that calcium free medium is used for all procedures. Fusion procedures are modifications of those previously reported (Campbell et al., 1993, 1994 loc cit) and are as described in the relevant section below, alternatively the nucleus may be introduced by injection of the donor cell into the enucleated oocyte (Ritchie & Campbell, *J. Reprod. Fertil. Abstract Series* (5) 60 (1995)). The timing of these events is dependent upon the species, the following two protocols outline the use of in vivo matured ovine and in vitro matured bovine oocytes.

Example 3

Ovine Nuclear Transfer 3.1 Superstimulation of Donor Ewes and Recovery of Oocytes Scottish Blackface ewes were synchronised with progestagen sponges for 14 days (Veramix™, Upjohn, UK) and induced to superovulate with single injections of 3.0 mg/day (total 6.0 mg) ovine follicle-stimulating hormone (FSH) (Ovagen™, Immuno-chemical Products Ltd, New Zealand) on two successive days. Ovulation was induced with an 8 mg single dose of a gonadotropin-releasing hormone analogue (GnRH Receptal™, Hoechst, UK) 24 hours after the second injection of FSH.

Unfertilised metaphase II oocytes were recovered by flushing from the oviduct at 24-29 hours after GnRH injection using Dulbecco's phosphate buffered saline containing 1.0% foetal calf serum (FCS) maintained at 37° C. until use.

3.2 Oocyte Manipulation

Recovered oocytes were maintained at 37° C., washed in PBS 1.0% FCS and transferred to calcium free M2 medium containing 10% Foetal Calf Serum (FCS), at 37° C. To remove the chromosomes, (enucleation) oocytes were placed in calcium free M2 containing 10% FCS, 7.5 µg/ml cytochalasin B (Sigma) and 5.0 µg/ml Hoechst 33342 (Sigma) at 37° C. for 20 minutes. A small amount of cytoplasm from directly beneath the 1st polar body was then aspirated using a 20 µM glass pipette. Enucleation was confirmed by exposing the aspirated portion of cytoplasm to UV light and checking for the presence of a metaphase plate.

3.3 Embryo Reconstruction

Groups of 10-20 oocytes were enucleated and placed into 20 µl drops of calcium free M2 medium at 37° C. 5% $CO_2$ under mineral oil (SIGMA). Each of the following three protocols (a), (b) and (c) were used for embryo reconstruction.

(a) "MAGIC" (Metaphase Arrested G1/G0 Accepting Cytoplast)

As soon as possible after enucleation a single cell was placed into contact with the oocyte by using a glass pipette to transfer the cell through the hole previously made in the zona pellucida. The cytoplast/cell couplet was then transferred into the fusion chamber in 200 µl of 0.3M mannitol in distilled water and manually aligned between the electrodes. An AC pulse of 5V was applied for 3 seconds followed by 3 DC pulses of 1.25 kV/cm for 80 µsecs. The couplets were then washed in calcium free M2, 10% FCS at 37° C. and incubated in the same medium under oil at 37° C. 5% $CO_2$. 30 minutes prior to activation the couplets were transferred to calcium free M2 medium 10% FCS containing 5 µM nocodazole. Activation was induced at 32-34 hours post hCG injection as described below. Following activation the reconstructed zygotes were incubated in medium TC199 (Gibco) 10% FCS at 37° C. 5% $CO_2$ for a further 3 hours. They were then washed 3 times for 5 minutes at 37° C. in the same medium without nocodazole and cultured for a further 12-15 hours prior to transfer to temporary recipient ewes.

(b) "GOAT" (G0/G1 Activation and Transfer)

At 32-34 hours post hCG injection a single cell was placed into contact with the enucleated oocyte. The couplet was transferred to the fusion chamber (see below) in 200 µl of 0.3M mannitol, 0.1 mM $MgSO_4$, 0.001 mM $CaCl_2$ in distilled water. Fusion and activation were induced by application of an AC pulse of 3V for 5 seconds followed by 3 DC pulses of 1.25 kV/cm for 80 µsecs. Couplets were then washed in TC199 10% FCS containing 7.5 µg/ml cytochalasin B and incubated in this medium for 1 hour at 37° C. 5% $CO_2$. Couplets were then washed in TC199 10% FCS and cultured for a further 12-15 hours in TC199 10% FCS at 37° C. 5% $CO_2$.

(c) "Universal Recipient"

Enucleated oocytes were activated (as described below) 32-34 hours post hCG injection and then cultured in TC199 10% FCS at 37° C. 5% $CO_2$ for 4-6 hours. A single cell was then placed into contact with the oocyte and fusion induced as described below. The couplets were then incubated in TC199 10% FCS 7.5 µg cytochalasin B for 1 hour at 37° C. 5% $CO_2$. Couplets were then washed and cultured in TC199 10% FCS at 37° C. 5% $CO_2$ for a further 8-11 hours.

3.4 Fusion and Activation

For activation, oocytes were placed between two parallel electrodes in 200 µl of 0.3M mannitol, 0.1 mM $MgSO_4$, 0.001 mM $CaCl_2$ in distilled water (Willadsen, Nature 320 63-65 (1986)). Activation was induced by application of 1 DC pulse of 1.25 kV/cm for 80 µs. For fusion, manipulated embryos were treated in a similar manner with the addition that the contact surface between the enucleated oocyte and the cell was arranged parallel to the electrodes. Fusion was induced by application of an AC current of 3V for 5 seconds followed by 3 DC pulses of 1.25 kV/cm for 80 µs.

3.5 Embryo Culture and Assessment (All Groups)

After the culture period fused couplets were double embedded in 1% and 1.2% agar (DIFCO) in PBS and transferred to the ligated oviduct of unsynchronised ewes. The couplet is embedded in agar to prevent or reduce immune rejection of the embryo by the recipient ewe and to assist in holding the couplet together. After 6 days recipient ewes were sacrificed and the embryos retrieved by flushing from the oviduct using PBS 10% FCS. Embryos were dissected from the agar chips using 2 needles and development assessed by microscopy. All embryos which had developed to the morula/blastocyst stage were transferred as soon as possible to the uterine horn of synchronised final recipient ewes.

In vitro techniques may also be suitable in place of a temporary recipient ewe to achieve development of the embryo to the blastocyst stage.

Example 4

Bovine Nuclear Transfer

4.1 In Vitro Oocyte Maturation

Ovaries were obtained from a local abattoir and maintained at 28-32° C. during transport to the laboratory. Cumulus oocyte complexes (COC's) were aspirated from follicles 3-10 mm in diameter using a hypodermic needle (1.2 mm internal diameter) and placed into sterile plastic universal containers. The universal containers were placed into a warmed chamber (35° C.) and the follicular material allowed to settle for 10-15 minutes before pouring off three quarters of the supernatant. The remaining follicular material was diluted with an equal volume of dissection medium (TCM 199 with Earles salts (Gibco), 75.0 mg/l kanamycin, 30.0 mM Hepes, pH 7.4, osmolarity 280 mOsmols/Kg $H_2O$) supplemented with 10% bovine serum, transferred into an 85 mm petri dish and searched for COC's under a dissecting microscope. Complexes with at least 2-3 compact layers of cumulus cells were selected washed three times in dissection medium and transferred into maturation medium (TC medium 199 with Earles salts (Gibco), 75 mg/l kanamycin, 30.0 mM Hepes, 7.69 mM $NaHCO_3$, pH 7.8, osmolarity 280 mOsmols/Kg $H_2O$) supplemented with 10% bovine serum and $1 \times 10^6$ granulosa cells/ml and cultured until required on a rocking table at 39° C. in an atmosphere of 5% $CO_2$ in air.

4.2 Oocyte Manipulation

Matured oocytes were stripped of cumulus cells 18 hours after the onset of maturation. Denuded oocytes were then washed in calcium free M2 medium containing 10% Foetal Calf Serum (FCS) and maintained in this medium at 37° C. To remove the chromosomes (enucleation) oocytes were placed in calcium free M2 containing 10% FCS, 7.5 ug/ml cytochalasin B (Sigma) and 5.0 ug/ml Hoechst 33342 (Sigma) at 37° C. for 20 minutes. A small amount of cytoplasm from directly beneath the 1st polar body was then aspirated using a 20 μM glass pipette. Enucleation was confirmed by exposing the aspirated portion of cytoplasm to UV light and checking for the presence of a metaphase plate.

4.3 Embryo Reconstruction

Enucleated oocytes were then used for each of the three methods of reconstruction (a), (b) and (c) as detailed below.

(a) "MAGIC" (Metaphase Arrested G1/G0 Accepting Cytoplast)

Enucleated oocytes were maintained in calcium free M2 10% FCS at 39° C. as soon as possible after enucleation, a single cell was placed into contact with the oocyte by using a glass pipette to transfer the cell through the hole previously made in the zona pellucida. The cytoplast/cell couplet was then transferred into the fusion chamber in 200 μl of 0.3M mannitol in distilled water. The couplet, was manually aligned between the electrodes. An AC pulse of 3V was applied for 5 seconds followed by 3 DC pulses of 1.25 kV/cm for 80 μsecs. The couplets were then washed in calcium free M2, 10% FCS at 37° C. and incubated in the same medium under oil at 37° C. 5% $CO_2$. 30 minutes prior to activation the couplets were transferred to calcium free M2 medium 10% FCS containing 5 μM nocodazole. Activation was induced as described below, following activation the reconstructed zygotes were incubated in medium TC199 10% FCS at 37° C. 5% $CO_2$ for a further 3 hours. They were then washed 3 times for 5 minutes at 37° C. in the same medium without nocodazole and cultured for a further 12-15 hours prior to transfer to temporary recipient ewes (ewes are a less expensive alternative as a temporary recipient for the reconstructed embryo).

(b) "GOAT" (G0/G1 Activation and Transfer)

Enucleated oocytes were returned to the maturation medium. At 30 or 42 hours post onset of maturation a single cell was placed into contact with the enucleated oocyte. The couplet was transferred to the fusion chamber (see below) in 200 μl of 0.3M mannitol, 0.1 mM $MgSO_4$, 0.001 mM $CaCl_2$ in distilled water. Fusion and activation were induced by application of an AC pulse of 3V for 5 seconds followed by 3 DC pulses of 1.25 kV/cm for 80 μsecs. Couplets were then washed in TC199 10% FCS and incubated at 37° C. 5% $CO_2$ for 15-20 hours (30 hpm group) or 4-8 hours (42 hpm group) [The abbreviation "hpm" is standard for "hours post-maturation"].

(c) "Universal Recipient"

Enucleated oocytes were activated (as described below) 30 or 42 hours post onset of maturation and then cultured in TC199 10% FCS at 37° C. 5% $CO_2$ for 8-10 hours (30 hpm group) or 4-6 hours (42 hpm group). A single cell was then placed into contact with the oocyte and fusion induced as described below. The couplets were then cultured in TC199 10% FCS at 37° C. 5% $CO_2$ for a further 12-16 hours (30 hpm group) or 4-6 hours (42 hpm group).

4.4 Fusion and Activation

For activation, oocytes were placed between two parallel electrodes in 200 μl of 0.3M mannitol, 0.1 mM $MgSO_4$, 0.001 mM $CaCl_2$ in distilled water (Willadsen, *Nature* 320 63-65 (1986)). Activation was induced by application of 1 DC pulse of 1.25 kV/cm for 80 μs. For fusion, manipulated embryos were treated in a similar manner with the addition that the contact surface between the enucleated oocyte and the cell was arranged parallel to the electrodes. Fusion was induced by application of an AC current of 3V for 5 seconds followed by 3 DC pulses of 1.25 kV/cm for 80 μs.

4.5 Embryo Culture and Assessment (All Groups)

After the culture period fused couplets were double embedded in 1% and 1.2% agar (DIFCO) in PBS and transferred to the ligated oviduct of unsynchronised ewes (ewes are a less expensive alternative as a temporary recipient for the reconstructed embryo). The couplet is embedded in agar to prevent or reduce immune rejection of the embryo by the recipient ewe and to assist in holding the couplet together. After 6 days recipient ewes were sacrificed and the embryos retrieved by flushing from the oviduct using PBS 10% FCS. Embryos were dissected from the agar chips using 2 needles and development assessed by microscopy.

In vitro techniques may also be suitable in place of a temporary recipient ewe to achieve development of the embryo to the blastocyst stage.

Results of Example 3 (Ovine Cells) and Example 4 (Bovine Cells

The present techniques have been applied to both ovine and bovine embryo reconstruction. At the present time blastocyst stage embryos have been obtained in cattle; however, no transfers of these embryos to final recipients have been performed. In sheep 7 recipient ewes became pregnant resulting in the birth of 5 live lambs (2 of which died shortly after birth). The results from these experiments are summarised in Tables 1-3.

Table 1 shows the results of development to blastocyst stage of ovine embryos reconstructed using quiescent TNT4 cell populations and 3 different cytoplast recipients. Reconstructed embryos were cultured in the ligated oviduct of a temporary recipient ewe until Day 7 after reconstruction. The results are expressed as the percentage of morula/blastocyst stage embryos in relation to the total number of embryos recovered.

TABLE 1

| DATE OF NUCLEAR TRANSFER | PASSAGE NUMBER | NUMBER MORULAE, BLASTOCYSTS/TOTAL NUMBER OF COUPLETS RECOVERED | | |
|---|---|---|---|---|
| | | "GOAT" | "MAGIC" | "UNIVERSAL" |
| 17.1.95 | 6 | 6/32 | 4/28 | |
| 19.1.95 | 7 | 1/26 | 1/10 | |
| 31.1.95 | 13 | | 0/2 | 2/14 |
| 2.2.95 | 13 | 0/11 | 0/14 | |
| 7.2.95 | 11 | | 1/9 | 0/9 |
| 9.2.95 | 11 | 9/29 | 1/2 | |
| 14.2.95 | 12 | | | 6/45 |
| 16.2.95 | 13 | | 3/13 | |
| TOTAL | | 16/98 (16.3%) | 10/78 (12.8%) | 8/68 (11.7%) |

Table 2 shows the results of induction of pregnancy following transfer of all morula/blastocyst stage reconstructed embryos to the uterine horn of synchronised final recipient blackface ewes. The Table shows the total number of embryos from each group transferred and the frequency of pregnancy in terms of ewes and embryos (in the majority of cases 2 embryos were transferred to each ewe. A single twin pregnancy was established using the "MAGIC" cytoplast.

TABLE 2

| PASSAGE NUMBER | "MAGIC" | "GOAT" | "UNIVERSAL" |
|---|---|---|---|
| P6 | 4 | 6 | 0 |
| P7 | 1 | 1 | 0 |
| P11 | 2 | 9 | 0 |
| P12 | 0 | 0 | 6 |
| P13 | 3 | 0 | 2 |
| TOTAL MOR/BL | 10 | 16 | 8 |
| TOTAL NUMBER EWES | 6 | 9 | 4 |
| PREGNANT EWES % | 1 (16.7) | 5 (55.5) | 1 (25.0) |
| FOETUSES/TOTAL TRANSFERRED (%) | 2/10 (20.0) | 5/16 (31.25) | 1/8 (12.5) |

Table 3 shows the outcome of the pregnancies established following transfer or morula/blastocyst stage embryos to final recipient ewes.

TABLE 3

| EWE | Method | Passage | Result |
|---|---|---|---|
| 4E468 | GOAT | 6 | LIVE LAMB |
| 4E302 | GOAT | 7 | FOETUS DIED (APPROX 130 DAYS) |
| 4E210 | GOAT | 11 | LIVE LAMB |
| 4E286 | GOAT | 11 | LIVE LAMB (DIED SHORTLY AFTER BIRTH) |
| 4E453 | GOAT | 11 | FOETUS DIED (APPROX 80 DAYS) |
| 4E294 | UNIVERSAL | 11 | LIVE LAMB |
| 4E272 | MAGIC | 13 | LIVE LAMB (DIED SHORTLY AFTER BIRTH) |

Example 5

Ovine Nuclear Transfer and Embryo Reconstruction Using OME, BLWF1 and SEC1 Cells Nuclear transfer has been conducted using three new cell types, designated OME, BLWF1 and SEC1. OME (ovine mammary epithelial) cells are an epithelial cell line established from a biopsy removed from the mammary gland of an adult 6 year old Fin-Dorset ewe, following the procedure of Finch et al., (*Biochem. Soc. Trans.* 24 369S (1996). BLWF1 (Black Welsh Fibroblast) cells are a fibroblast cell line obtained by dissection and culture of a day 26 Black Welsh foetus obtained following Natural Mating of a Black Welsh ewe to a Black Welsh tup. The method of isolation of primary, foetal fibroblasts is according to Robertson, E. J., in *Teratocarcinomas and embryonic stem cells: A practical approach*, 71-112, IRL Press Oxford (1987). SEC1 (Sheep embryonic Cell) are an epithelial-like cell line derived from a day 9 embryo obtained from a super ovulated and mated Pol-Dorset ewe to a Pol-Dorset tup. The SEC1 cells are distinct from the TNT cells described in co-pending PCT application No. PCT/GB95/02095 published as WO 96/07732 for the following reasons. Firstly, the morphology of the cells of the two cell lines are completely different and secondly, the methods used to isolate the cell lines were different. The SEC1 cell line was established from a single embryo whereas the TNT cell lines are derived from groups of cells.

All cell lines were karyotyped and showed a modal chromosome number of 54 (2n). Prior to use as nuclear donors for embryo reconstruction, the induction of quiescence following the reduction of serum levels to 0.5% was monitored as previously described (Campbell et al., *Nature* 380 64-66 (1996)). Preparation of the reconstructed embryos was as described above in the previous examples.

Table 4 shows a summary of the development of nuclear transfer embryos reconstructed from different cell types. The table shows the number of embryos reconstructed, development to the blastocyst stage and number of pregnancies for each of the three cell types. All cell lines were karyotyped prior to their use for embryo reconstruction. These cell lines had a modal number of 54 chromosomes. One to three blastocyst stage embryos were transferred to each synchronised final recipient ewe. Reconstructed embryos which were cultured in vitro were placed into 10 µl (4 embryos) drops of SOFM (synthetic oviduct fluid medium) containing 10% human serum and cultured in a humidified atmosphere of 5% $O_2$, 5% $CO_2$ and 90% $N_2$ at 39° C. Cultured embryos were transferred to fresh medium every two days. SOFM medium was prepared according to Gardner et al., *Biology of Reproduction* 50 390-400 (1994) and Thompson et al., *Biology of Reproduction* 53 1385-1391 (1995).

Table 5 shows the identification of the recipient ewes remaining pregnant at 24 Jun. 1996, the cell type used for embryo reconstruction and the expected lambing date. Pregnancies were established by the transfer of 1 to 3 morula/blastocyst stage embryos (on day 7 after reconstruction) to synchronised final recipient ewes. Details of the numbers reconstructed are shown in Table 4. Abbreviations are: PD=Pol-Dorset, BW=Black Welsh, FD=Fin-Dorset, *=embryo cultured in vitro to the blastocyst stage.

TABLE 4

| Cell Type | No. of cytoplasts prepared | No. fused couplets (%) | No. couplets transferred to oviducts (in vitro cultured) | No. couplets recovered from oviduct (%) | No. Morula/Blastocyst stage (%) | No. pregnancies/No. Blastocyst (%) | No. pregnancies/No. recipient ewes (%) |
|---|---|---|---|---|---|---|---|
| OME | 387 | 277 (63.8) | 277 | 247 (89.2) | 29 (11.7) | 1/29 (3.4) | 1/13 (7.7) |
| BLWF1 | 203 | 172 (84.7) | 143 (24) | 124 (86.7) | 34 (27.4) | 4/34 (11.8) | 4/10 (40.0) |
| | | | | | 13 (54.2) | 1/6 (16.6) | 1/6 (16.6) |
| SEC1 | 465 | 385 (82.8) | 271 (92) | 231 (85.3) | 90 (39.0) | 14/72 (19.5) | 14/27 (51.8) |
| | | | | | 36 (39.0) | 1/15 (6.6) | 1/5 (20.0) |

TABLE 5

| I.D. of recipient ewe | Cell line | Outcome of pregnancy | Breed |
|---|---|---|---|
| 5E191 | SEC1 | LIVE LAMB (MALE) | PD |
| 5E17 | SEC1 | LIVE LAMB (MALE) | PD |
| 5E134 | SEC1 | DEAD LAMB (MALE) | PD |
| 9M399 | SEC1 | LIVE LAMB (MALE) | PD |
| 5E524 | SEC1 | LIVE LAMB (MALE) | PD |
| 5E139 | BLWF1 | LIVE LAMB (MALE) | BW |
| 5E328 | BLWF1 | LIVE LAMB (MALE) | BW |
| 5E169 | BLWF1 | LIVE LAMB (MALE) died at birth | BW |
| 5E475 | OME | LIVE LAMB (FEMALE) | FD |

The invention claimed is:

1. A method of cloning an ungulate comprising:
   (i) providing a reconstructed ungulate embryo comprising the nucleus from a quiescent, ungulate somatic cell, wherein said embryo is capable of cell division;
   (ii) transferring said embryo to a host ungulate of the same species; and
   (iii) developing said embryo to term.

2. The method of claim 1, wherein the ungulate is a bovine.

3. The method of claim 1, wherein the ungulate is a sheep.

4. The method of claim 1, wherein the ungulate is a goat.

5. The method of claim 1, wherein the ungulate is a pig.

6. The method of claim 1, further comprising culturing the embryo in vitro prior to transfer to the host.

7. The method of claim 1, further comprising culturing the embryo in vivo prior to transfer to the host.

8. The method of claim 1, wherein the somatic cell is a fibroblast cell.

9. The method of claim 1, wherein the somatic cell is a cultured cell.

10. The method of claim 1, wherein the somatic cell is a transgenic cell.

11. A method of preparing an ungulate embryo comprising:
    (i) providing a reconstructed ungulate embryo comprising a nucleus from a quiescent, ungulate somatic cell, wherein said embryo is capable of cell division; and
    (ii) culturing the embryo, wherein said cultured embryo is capable of developing to term.

12. The method of claim 11, wherein the ungulate is a bovine.

13. The method of claim 11, wherein the ungulate is a sheep.

14. The method of claim 11, wherein the ungulate is a goat.

15. The method of claim 11, wherein the ungulate is a pig.

16. The method of claim 11, comprising culturing the embryo in vitro.

17. The method of claim 11, comprising culturing the embryo in vivo.

18. The method of claim 11, wherein the somatic cell is a fibroblast cell.

19. The method of claim 11, wherein the somatic cell is a cultured cell.

20. The method of claim 11, wherein the somatic cell is a transgenic cell.

* * * * *